(12) United States Patent
Garcia et al.

(10) Patent No.: US 9,962,169 B2
(45) Date of Patent: *May 8, 2018

(54) SURGICAL DEVICE WITH SMART BIT RECOGNITION COLLET ASSEMBLY TO SET A DESIRED APPLICATION MODE

(71) Applicant: Zimmer Biomet CMF and Thoracic, LLC, Jacksonville, FL (US)

(72) Inventors: Saddy Garcia, St. Augustine, FL (US); Bradley Winterroth, Wesley Chapel, FL (US); Ryan Luby, Ponte Vedra Beach, FL (US); Larry Miller, Ponte Vedra Beach, FL (US); Christopher C. Dyer, Overland Park, KS (US); Benjamin J. Gray, Kansas City, MO (US); Allan J. Meredith, Olathe, KS (US)

(73) Assignee: Zimmer Biomet CMF and Thoracic, LLC, Jacksonville, FL (US)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/450,256

(22) Filed: Mar. 6, 2017

(65) Prior Publication Data

US 2017/0238941 A1    Aug. 24, 2017

Related U.S. Application Data

(60) Continuation of application No. 14/846,224, filed on Sep. 4, 2015, now Pat. No. 9,585,677, which is a
(Continued)

(51) Int. Cl.
*A61B 17/16* (2006.01)
*A61B 17/56* (2006.01)
(Continued)

(52) U.S. Cl.
CPC ........ *A61B 17/1626* (2013.01); *A61B 17/162* (2013.01); *A61B 17/1617* (2013.01);
(Continued)

(58) Field of Classification Search
CPC . A61B 17/1626; A61B 90/03; A61B 17/1617; A61B 17/162
See application file for complete search history.

(56) References Cited

U.S. PATENT DOCUMENTS

| | | |
|---|---|---|
| 2,414,882 A | 1/1947 | Longfellow |
| 3,926,264 A | 12/1975 | Bardwell et al. |

(Continued)

FOREIGN PATENT DOCUMENTS

| | | |
|---|---|---|
| DE | 19620782 A1 | 12/1996 |
| JP | 2002283248 A | 10/2002 |

OTHER PUBLICATIONS

"Answer to Plaintiff Intelligent Automation Design, LLC's First Amended Complaint", *Intelligent Automation Design, LLC, v. Zimmer Biomet CMF and Thoracic,LLC D/B/A Biomet Microfixation*, Case 3:16-cv-01044-BJD-MCR PageID 136-PageID 149, (Filed Apr. 7, 2016), 14 pgs.
(Continued)

*Primary Examiner* — Christian Sevilla
(74) *Attorney, Agent, or Firm* — Schwegman Lundberg & Woessner, P.A.

(57) ABSTRACT

A surgical device of a drill/driver with bit recognition to set a desired application mode and a method of utilization thereof is provided. Various operating modes of the drill/driver are automatically set by a sensor which recognizes the bit applied to the drill/driver. A method of utilizing the drill/driver allows the drill driver to apply surgical screws at
(Continued)

very high speeds while automatically preventing excessive torque levels that would strip out the surgical screw from the patient's bone.

11 Claims, 7 Drawing Sheets

Related U.S. Application Data continuation of application No. 13/965,692, filed on Aug. 13, 2013, now abandoned, which is a division of application No. 13/134,253, filed on Jun. 2, 2011, now Pat. No. 8,529,567.

(60) Provisional application No. 61/396,803, filed on Jun. 3, 2010.

(51) Int. Cl.
| | | |
|---|---|---|
| *A61B 17/86* | (2006.01) | |
| *A61B 90/00* | (2016.01) | |
| *A61B 17/88* | (2006.01) | |
| *A61B 90/98* | (2016.01) | |
| *B25B 21/00* | (2006.01) | |
| *B25B 23/00* | (2006.01) | |
| *B25B 23/147* | (2006.01) | |

(52) U.S. Cl.
CPC ...... *A61B 17/8625* (2013.01); *A61B 17/8875* (2013.01); *A61B 90/03* (2016.02); *A61B 90/98* (2016.02); *B25B 21/002* (2013.01); *B25B 23/0035* (2013.01); *B25B 23/147* (2013.01); *A61B 2090/031* (2016.02)

(56) References Cited

U.S. PATENT DOCUMENTS

| | | | |
|---|---|---|---|
| 3,962,910 | A | 6/1976 | Spryidakis |
| 4,095,325 | A | 6/1978 | Hashimoto et al. |
| 4,244,213 | A | 1/1981 | Marcinkiewicz |
| 4,249,117 | A | 2/1981 | Leukhardt et al. |
| 4,267,914 | A | 5/1981 | Saar |
| 4,273,198 | A | 6/1981 | Doniwa |
| RE31,569 | E | 5/1984 | Eshghy |
| 4,450,727 | A | 5/1984 | Reinholm et al. |
| 4,684,922 | A | 8/1987 | Minogue |
| 4,705,038 | A | 11/1987 | Sjostrom et al. |
| 4,721,169 | A | 1/1988 | Nagasawa et al. |
| 4,894,767 | A | 1/1990 | Doniwa |
| 4,908,926 | A | 3/1990 | Takeshima et al. |
| 4,995,877 | A | 2/1991 | Ams et al. |
| 5,014,793 | A | 5/1991 | Germanton |
| 5,038,084 | A | 8/1991 | Wing |
| 5,061,885 | A | 10/1991 | Fukuhara |
| 5,152,046 | A | 10/1992 | Abe |
| 5,154,242 | A | 10/1992 | Soshin et al. |
| 5,155,421 | A | 10/1992 | Hansson |
| 5,207,697 | A | 5/1993 | Carusillo et al. |
| 5,315,501 | A | 5/1994 | Whitehouse |
| 5,404,643 | A | 4/1995 | Rice |
| 5,410,229 | A | 4/1995 | Sebastian et al. |
| 5,496,330 | A | 3/1996 | Bates et al. |
| 5,563,482 | A | 10/1996 | Shaw et al. |
| 5,591,919 | A | 1/1997 | Hathaway et al. |
| 5,626,474 | A | 5/1997 | Kukla et al. |
| 5,632,759 | A | 5/1997 | Rexroth |
| 5,637,968 | A | 6/1997 | Kainec et al. |
| 5,993,454 | A | 11/1999 | Longo |
| 6,110,174 | A | 8/2000 | Nichter |
| 6,132,435 | A | 10/2000 | Young |
| 6,171,312 | B1 | 1/2001 | Beaty et al. |
| RE37,358 | E | 9/2001 | Del Rio et al. |
| 6,329,778 | B1 | 12/2001 | Culp et al. |
| 6,378,623 | B2 | 4/2002 | Kawarai |
| 6,402,757 | B1 | 6/2002 | Moore, III et al. |
| 6,479,958 | B1 | 11/2002 | Thompson et al. |
| 6,516,896 | B1 | 2/2003 | Bookshar et al. |
| 6,676,665 | B2 | 1/2004 | Foley et al. |
| 6,680,595 | B2 | 1/2004 | Ito |
| 6,700,341 | B2 | 3/2004 | Schaer et al. |
| 6,780,175 | B1 | 8/2004 | Sachdeva et al. |
| 7,091,683 | B1 * | 8/2006 | Smith ................ A61B 17/8875 173/176 |
| 7,507,231 | B2 | 3/2009 | Schmieding et al. |
| 7,823,465 | B2 | 11/2010 | Makimae et al. |
| 8,485,075 | B1 | 7/2013 | Gauthier et al. |
| 8,529,567 | B2 | 9/2013 | Garcia et al. |
| 9,585,677 | B2 | 3/2017 | Garcia et al. |
| 2003/0121685 | A1 | 7/2003 | Yamamoto |
| 2005/0131415 | A1 * | 6/2005 | Hearn ................ A61B 17/1626 606/80 |
| 2005/0205274 | A1 | 9/2005 | Bogue |
| 2006/0117911 | A1 | 6/2006 | Raines, Jr. et al. |
| 2007/0060933 | A1 | 3/2007 | Sankaran et al. |
| 2007/0191915 | A1 | 8/2007 | Strother et al. |
| 2008/0060487 | A1 | 3/2008 | Schell |
| 2008/0215060 | A1 | 9/2008 | Garcia et al. |
| 2008/0221564 | A1 | 9/2008 | Rouiller et al. |
| 2013/0025892 | A1 | 1/2013 | Mashiko et al. |
| 2013/0098646 | A1 | 4/2013 | Funabashi et al. |
| 2016/0030058 | A1 | 2/2016 | Garcia et al. |

OTHER PUBLICATIONS

"U.S. Appl. No. 13/134,253, Notice of Allowance dated May 13, 2013", 13 pgs.

"U.S. Appl. No. 13/134,253, Preliminary Amendment filed Jun. 3, 2011", 4 pgs.

"U.S. Appl. No. 13/134,253, Response filed Mar. 1, 2013 to Restriction Requirement dated Dec. 3, 2012", 3 pgs.

"U.S. Appl. No. 13/134,253, Restriction Requirement dated Dec. 3, 2012", 8 pgs.

"U.S. Appl. No. 13/965,692, Non Final Office Action dated Mar. 9, 2015", 9 pgs.

"U.S. Appl. No. 14/846,224, Non Final Office Action dated Mar. 7, 2016", 7 pgs.

"U.S. Appl. No. 14/846,224, Notice of Allowance dated Oct. 24, 2016", 5 pgs.

"U.S. Appl. No. 14/846,224, Response filed Aug. 5, 2016 to Non Final Office Action dated Mar. 7, 2016", 8 pgs.

"Chinese Application Serial No. 201120194609.9, Office Action dated Feb. 8, 2012", (W/ English Translation), 7 pgs.

"Declaration of Brian Gore", *Zimmer Biomet CMF and Thoracic, LLC v. Intelligent Automation Design, LLC* Inter Partes Review No. Unassigned Petition for Inter Partes Review for U.S. Pat. No. 7,091,683, (Filed Jan. 18, 2017), 148 pgs.

"European Application Serial No. 11168733.1, Communication Pursuant to Article 94(3) EPC dated Jul. 1, 2016", 4 pgs.

"European Application Serial No. 11168733.1, Communication Pursuant to Article 94(3) EPC dated Oct. 26, 2015", 4 pgs.

"European Application Serial No. 11168733.1, Extended European Search Report dated Sep. 23, 2011", 6 pgs.

"European Application Serial No. 11168733.1, Response filed Mar. 7, 2016 to Communication Pursuant to Article 94(3) EPC dated Oct. 26, 2015", 11 pgs.

"European Application Serial No. 11168733.1, Response filed Jun. 7, 2012 to Extended European Search Report dated Sep. 23, 2011", 20 pgs.

"European Application Serial No. 11168733.1, Response filed Nov. 7, 2016 to Communication Pursuant to Article 94(3) EPC dated Jul. 1, 2016", 12 pgs.

"Patent Owner's Preliminary Response Under 37 C.F.R. § 42.107", *Zimmer Biomet CMF and Thoracic, LLC, v. Intelligent Automation Design, LLC,* IPR2017-00727 U.S. Pat. No. 7,091,683, (Filed May 8, 2017), 69 pgs.

"Petition for Inter Partes Review of U.S. Pat. No. 7,091,683", *Zimmer Biomet CMF and Thoracic, LLC v. Intelligent Automation Design, LLC* Inter Partes Review No. Unassigned, (Filed Jan. 18, 2017), 83 pgs.

(56) References Cited

OTHER PUBLICATIONS

"Plaintiff's First Amended Complaint", *Intelligent Automation Design, LLC*, v. *Zimmer Biomet CMF and Thoracic, LLC d/b/a Biomet Microfixation*, Case No. 5:16-cv-00011-JRG-CMC, Case 3:16-cv-01044-BJD-MCR, (Filed Mar. 24, 2016), 6 pgs.

"Plaintiff's Original Complaint", *Intelligent Automation Design, LLC*, v. *Zimmer Biomet Holdings, Inc., Biomet, Inc.* Case 3:16-cv-01044-BJD-MCR, (Filed Jan. 14, 2016), 6 pgs.

Brockwell, Peter J., et al., "Introduction to Time Series and Forecasting", Second Edition, Springer, Zimmer Biomet CMF and Thoracic, LLC Exhibit 1032, p. 1-4 Section 1.5 Estimation and Elimination of Trend and Seasonal Components, (2002), 4 pgs.

Brown, Robert Goodell, "Smoothing, Forecasting and Prediction of Discrete Time Series", Zimmer Biomet CMF and Thoracic, LLC Exhibit 1033, p. 1-33, (1962), 33 pgs.

Gill, P.J., "The Yielding of Fastenings During Tightening", The Japan Research Institute for Screw Threads and Fasteners vol. 7 No. 12—Zimmer Biomet CMF and Thoracic, LLC Exhibit 1034, p. 1-11 w/ English Translation, (1976), 11 pgs.

Hsu, Yeh-Liang, et al., "A Modular Mechatronic System for Automatic Bone Drilling", Biomedical Engineeringapplications, Basis & Communications vol. 13 No. 4 Zimmer Biomet CMF and Thoracic, LLC Exhibit 1037, pp. 1-7, (Aug. 2001), 168-174.

Sears, Francis W., et al., "University Physics", Zimmer Biomet CMF and Thoracic, LLC Exhibit 1022, p. 1-4 Referencing Section 12-4 Elasticity and Plasticity, (1987), 4 pgs.

Smith, Steven W., "The Scientist and Engineer's Guide to Digital Signal Processing", Zimmer Biomet CMF and Thoracic, LLC Exhibit 1030, p. 1-16 Chapter 19—Recursive Filters, (1999), 16 pgs.

Wadsworth, Harrison M., "Handbook of Statistical Methods for Engineers and Scientists", McGraw-Hill, Zimmer Biomet CMF and Thoracic, LLC Exhibit 1031, p. 1-17, Section 19.26-19.35, (1998), 17 pgs.

* cited by examiner

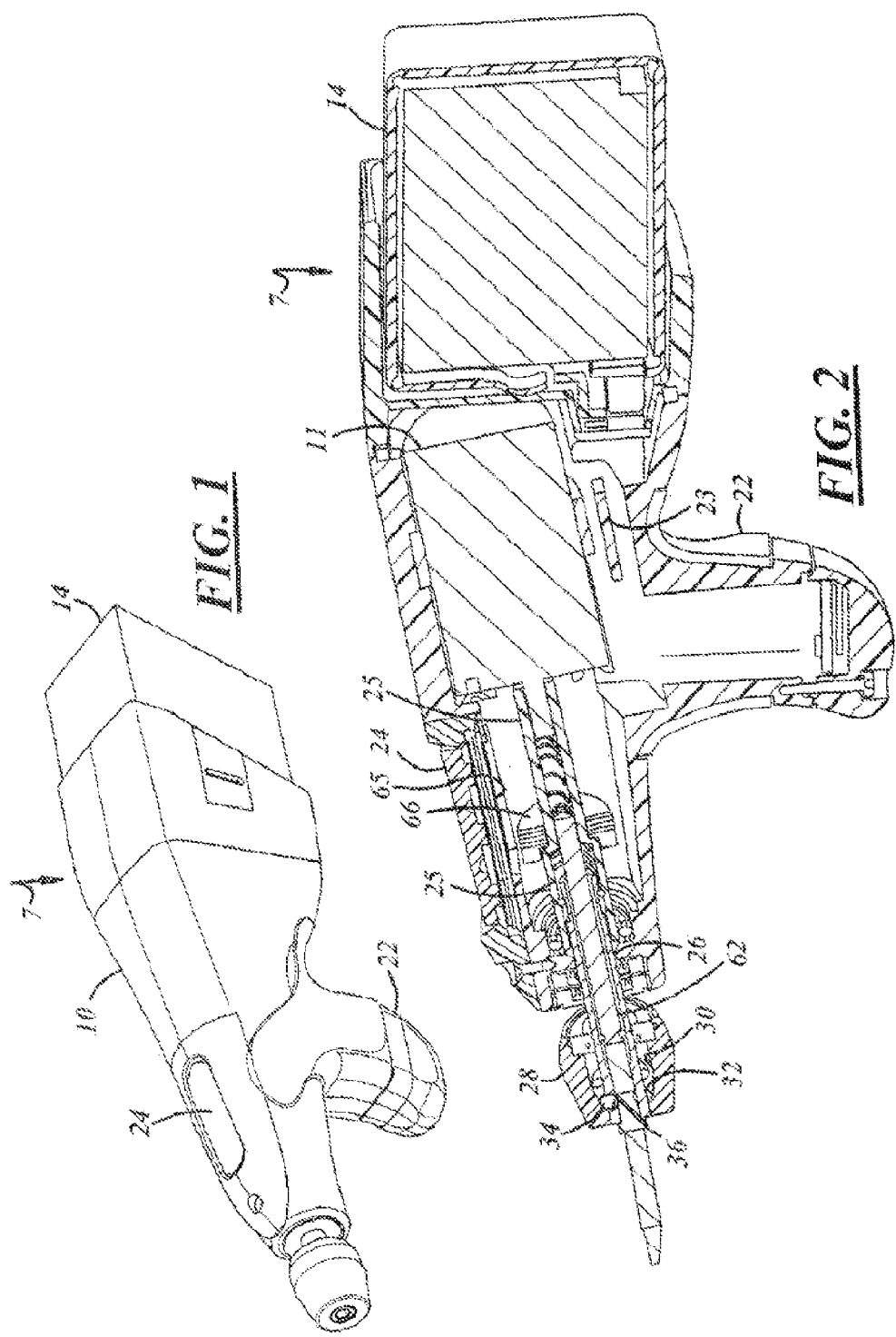

SURGICAL DEVICE WITH SMART BIT RECOGNITION COLLET ASSEMBLY TO SET A DESIRED APPLICATION MODE

CROSS-REFERENCE TO RELATED APPLICATIONS

This application is a continuation of U.S. patent application Ser. No. 14/846,224 filed Sep. 4, 2015, which is a continuation of U.S. patent application Ser. No. 13/965,692 filed Aug. 13, 2013 which is a divisional of and claims the benefit of U.S. patent application Ser. No. 13/134,253 filed on Jun. 2, 2011, now issued as U.S. Pat. No. 8,529,567, which claims the benefit of U.S. Provisional Patent Application No. 61/396,803, filed Jun. 3, 2010. The disclosures of the above applications are incorporated herein by reference.

FIELD OF THE INVENTION

The present invention relates to methods of securing a threaded fastener into a patient's body and to a surgical drill/driver utilized for inserting and torquing a surgical screw into a patient's body.

BACKGROUND OF THE INVENTION

Surgical screws are utilized for various purposes in surgical operations. Surgical screws are utilized for repairing fractures in bones or for attaching prosthesis to a bone. Surgical screws are also utilized for plates connected with a patient's body either permanently or temporarily after an operation. When using a surgical drill/driver in an operating environment, it is desirable that the drill/driver torque the screw within the patient's body in the safest, most efficient manner possible.

In many facial or cranial operations, a plate is utilized to stabilize two sections of bone after completion of the operation. Prior to the present invention, typically a hole was drilled into the patient's bone with a surgical drill/driver. A self-tapping surgical screw was then torqued into the hole by hand by the surgeon. In an alternate method, a self drilling surgical screw was utilized. The surgeon, buy virtue of their experience and tactile touch, was careful not to over torque the surgical screw. Over torquing the surgical screw could thereby cause a strip out of the threads that were created within the patient's bone mass.

Although hand torquing threaded surgical screws to attach a plate to a patient's bone is efficient, there are certain undesirable conditions that can occur. Hand torquing a surgical screw can provide a less than optimal result due to the inherent wobble in the rotational axis of the axis of a screw driver when the screw driver is turned manually. Even in the hands of the most skilled surgeon, some wobble typically occurs. Secondly, strip out of the threads formed in the bone by over torquing the surgical screw is primarily dependent upon the skill of the surgeon. Thirdly, it is desirable to torque the surgical screw and associated plate to the patient's body in a method that additionally requires less effort by the surgeon. Fourthly, it is desirable to complete torquing of the surgical screw to the patient in less time than a manual torquing procedure.

To improve upon the manual operation of torquing a surgical screw into a patient's bone to secure a plate to patient's body, various powered surgical drills/drivers have been developed. Most of the surgical drill/drivers are electrically and preferably battery powered. One of the major advantages of the electrically powered drill/driver is that the axis of torque remains constant during the torquing operation and therefore the wobble inherent in manual operation by the surgeon is eliminated. However, with the mechanized torquing of the surgical screw into the patient's bone, there is a lack of tactical feedback to the surgeon to alert the surgeon that further torquing operation can inadvertently cause a strip out of the threads formed within the bone matter of the patient.

Prior manual bone screw insertion techniques typically require three to five seconds. To reduce the time required, there has been trend to go toward aforementioned mechanical drill/drivers. However, increasing the speed on a mechanical drill/driver increases the chances of an inadvertent strip out of the formed threads in the patient's bone matter. It is desirable to provide a drill/driver and a method of utilizing the same wherein strip out of the threads formed in the patient's bone can be prevented while allowing the drill/driver to operate to connect a surgical screw with a patient within time segments as short as 45 ms (actual screw insertion time varies dependent upon the size of the screw). Additionally, it is also desirable to provide a drill/driver that has a form of bit recognition to allow the surgical drill/driver to override a manual command signal to the drill/driver when the manually commanded signal of the drill/driver is outside a desired operational parameter for the drill bit or driver bit that is connected with the surgical drill/driver.

SUMMARY OF THE INVENTION

To make manifest the above noted and other manifold desires, a revelation of the present invention is brought forth. In a preferred embodiment, the present invention provides a surgical drill/driver wherein various operating modes of the drill/driver are automatically set by a controller that recognizes a bit applied to the drill/driver. Additionally, a preferred embodiment of the present invention provides a method of utilizing the above noted drill/driver that allows the drill/driver to apply surgical screws at very high speeds while automatically preventing excessive torque levels that can rip out the surgical screw from the patient's bone matter.

Other advantages of the present invention will become more apparent to those skilled in the art from a review of the invention as it is provided in the accompanying drawings and detailed description.

BRIEF DESCRIPTION OF THE DRAWINGS

The present invention will become more fully understood from the detailed description and the accompanying drawings, wherein:

FIG. 1 is a perspective view of a surgical drill/driver according to the present invention;

FIG. 2 is a perspective sectional view of the drill/driver shown in FIG. 1;

DETAILED DESCRIPTION OF THE PREFERRED EMBODIMENTS

The following description of the preferred embodiment(s) is merely exemplary in nature and is in no way intended to limit the invention, its application, or uses.

Figure 3:
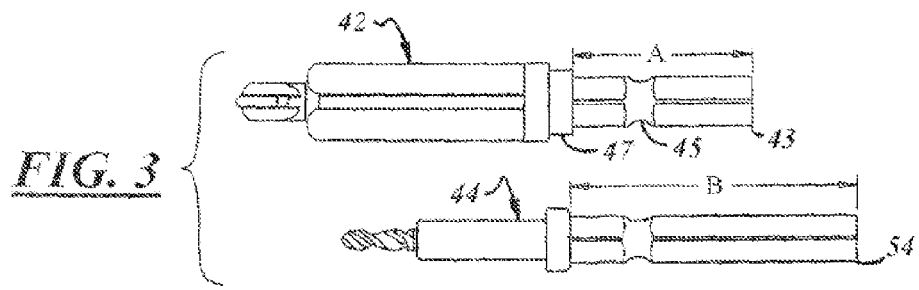
FIG. 3 is a perspective view of various drill and driver bits utilized with the drill/driver shown in FIGS. 1 and 2.
Figure 4:
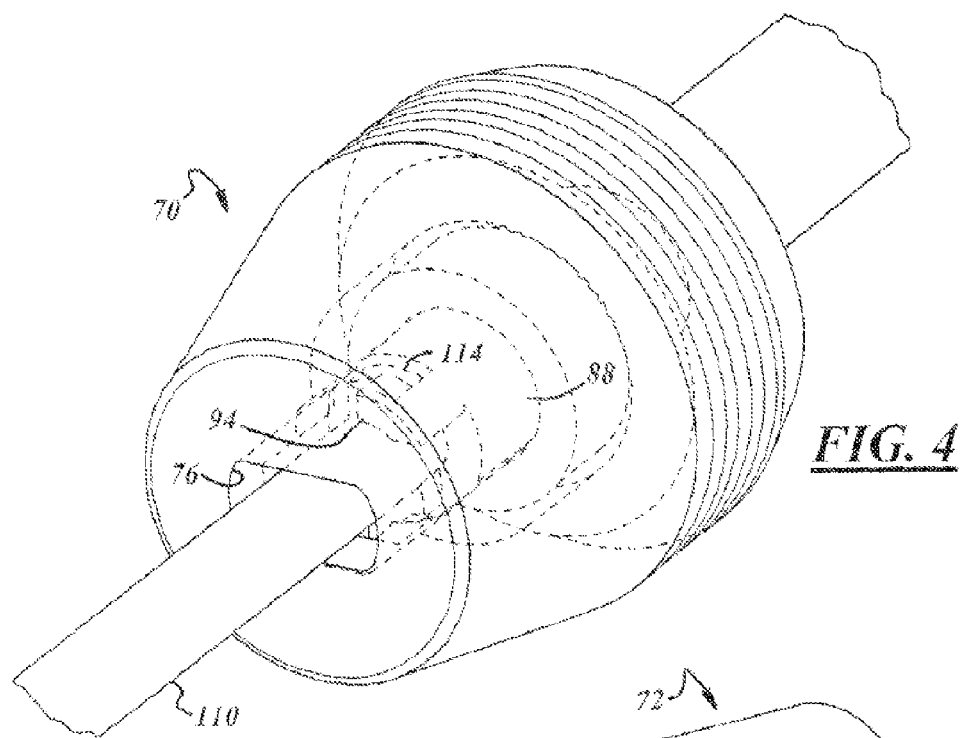
FIG. 4 is an enlarged perspective view of an alternative arrangement collett for the drill/driver according to the present invention.
Figure 5:
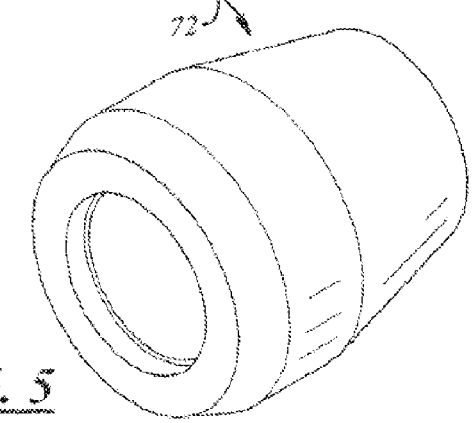
FIG. 5 is a rear perspective view of a front portion of a collett shown in FIG. 4.
Figure 6:
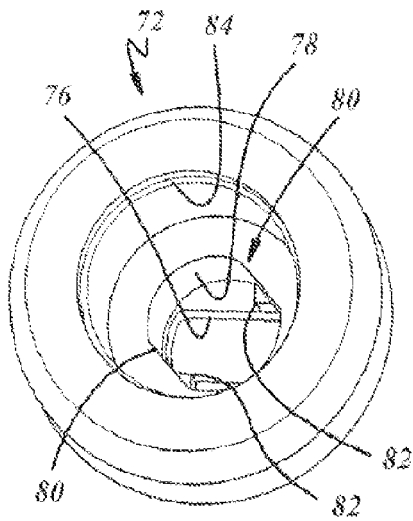
FIG. 6 is another rear perspective view of the front portion of a collett shown in FIG. 4.
Figure 8:
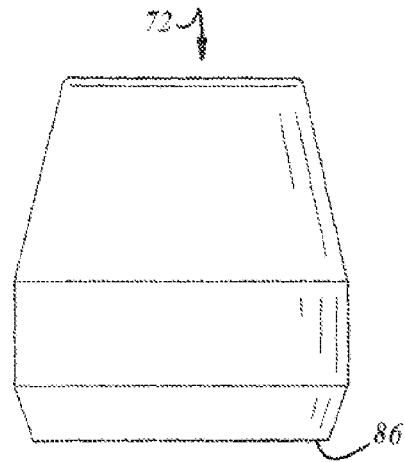
FIG. 8 is a side elevation view of the front portion of the collett shown in FIG. 4.
Figure 7:
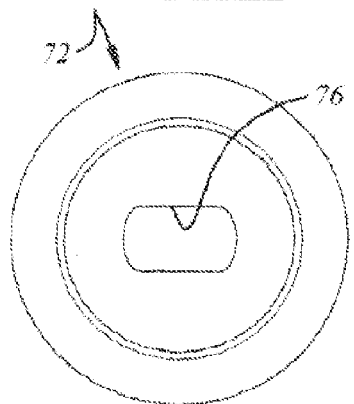
FIG. 7 is a front view of the front portion of the collett shown in FIG. 4.
Figure 10:
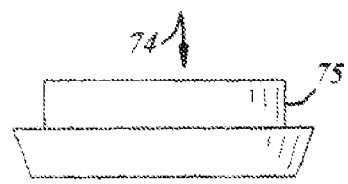
FIG. 10 is a side elevation view of the rear portion of the collett shown in FIG. 4.
Figure 9:
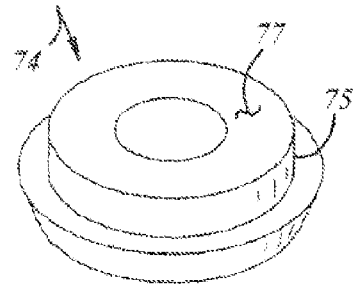
FIG. 9 is a perspective view of a rear portion of the collett shown in FIG. 4.
Figure 11:
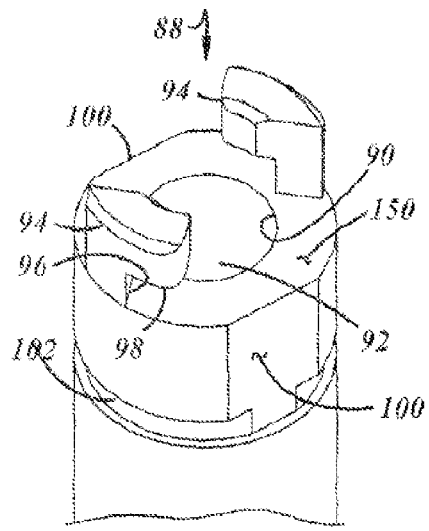
FIG. 11 is an enlarged perspective view of a front portion of a tubular shaft utilized with the collett of FIG. 4.

Referring to FIGS. 1, 2 and 3, a multiple use surgical drill/driver assembly 7 with a smart bit recognition system is provided. The surgical drill/driver 7 has a drill body 10. The drill body 10 is typically fabricated from a metal or polymeric material. The drill body 10 in its rearward end is connected with a battery pack 14 to allow the surgical drill/driver 7 to function without a power cord.

The drill body 10 mounts a brushless motor 11. The motor 11 typically has a nominal 20 watt output with a stall torque of 195 m Nm and has a variable (no load) speed to 35,500 rpm. A large portion of the control electronics are located on a circuit board 23 located under the motor 11. The drill body 10 has a handle 22. An overhead manual control trigger 24 is responsive to an input of the surgeon. The trigger 24 provides a manual command signal to the motor 11.

The motor 11 drives an outer shaft 25. The outer shaft drives an inner shaft 26. At an extreme end of the inner shaft 26 is a collet connecter 28. A forward push on the collet 28 positions an enlarged portion 30 of a collet multiple inner diameter 32 to be adjacent to a retainer bearing ball 34 allowing the retainer ball to be pushed outwardly of its retainer aperture 36 in the inner shaft 26. Selectively connected with the collet 28 is a plurality of bits 42 and 44. The bit 42 is for a screw driver blade. The bit 44 is for a drill. The bit 44 is for a specific set of a titanium screw. Not shown are other bits that would be for other size screws or bioabsorbable screws. Typically the bit 42 functions for several sizes of titanium screws of various lengths and diameters. Each bit has a shank portion with a unique length that is measured from a flange 47 to the shank extreme end. The shank portion 43 for the bit 42 can have a length "A" of approximately 0.445 inches. The portion of the shank from the flange to an annular groove 45 that mates with the retaining bearing ball 34 is typically constant for all of the bits. Shank 54 provided for the drill bit 44 can have a length of approximately 0.563 inches. As explained later, the shank lengths are used to identify to a controller of the drill/driver 7 what bit is connected with the collet 28.

Slidably mounted within the inner shaft 26 is a plunger 62. The plunger 62 is spring loaded to make abutting contact with the shank of a bit connected with the collet 28. Through a slot (not shown) in the outer shaft 25, a set of reflector targets 66 are connected with the plunger 62. A positional sensor (or sensors) located on a bottom of a printed circuit board 65 underneath the trigger 24 determines an axial location of the plunger 62 by determining the position of targets 66. As mentioned previously, each bit has a portion with a unique length as an identifying characteristic. In an alternative embodiment (not shown) the identifying characteristic of the various bits can be electrical resistance, shank geometry or shape magnetic field strength of the shank, or radio frequency identification optical characteristics or often identifying characteristics. Desirable ranges of various operational parameter(s) specific to the identified bit are stored in a memory. The memory can communicate with a controller (typically located on a circuit board 23)

When a bit is connected with the drill/driver, predetermined desired operational parameters such as speed, torque levels, insertion rates and/or derivatives thereof, are alerted from the memory to the controller to control the operation of the drill/driver 7. A rotational speed sensor informs the controller of rotational speed data. Additionally other sensors may provide the controller with other operational parameter realized data. In certain conditions, the controller provides an override function. If the surgeon attempts to operate the drill or driver outside of the predetermined operation parameters for a given bit, the controller provides an override function to override the manual command signal provided by the surgeon. For example, when the drill/driver 7 is in the drill mode, the drill/driver can be provided with a timed automatic shut off (to prevent overheating of the motor 11). The turn off of the drill/driver 7 to prevent overheating is also programmed to be disabled whenever the controller determines that there is a torque level greater than 0 inch-ounces that informs the controller that the drill bit 44 is currently within bone material and therefore shutting off of the drill/driver 7 should not be allowed to prevent a drill bit 44 being stuck within a patients' bone matter.

Referring to FIGS. 4-15, an alternate embodiment collett and drill bit arrangement for the present invention is provided. Collett 70 has a front piece 72 and a rear closing end piece 74. The front piece 72 has a generally oblong window 76. An interior of the front piece 72 has a generally circular bore 78 with two chordal flats 80. Extending generally radially from a portion of the chordal flats 80 are two triangular stops 82. Rearward of the circular bore 78 is a spring chamber 84. The collett front piece has a rearward end 86. The collett rearward member 74 has an annular portion 75 which is fitted within the spring chamber 84 of the forward piece 72.

Powered by the motor 11 is a generally tubular shaft 88. The tubular shaft 88 has a central bore 90. Slidably axially mounted within the tubular bore 90 is a plunger 92. Connected on the front end of the tubular shaft 88 are two opposed hook stops 94. Each hook stop 94 has a nest 96 and an overlapping cantilever portion 98. Additionally, the tubular shaft 88 has two chordal flats 100 which are mated with the chordal flats 80 of the collett front piece to angularly retain the collett 70 with the shaft 88. The shaft 88 additionally has a C-ring groove 102 for installation of a C-ring (not shown) that retains a spring (not shown) that pushes against the C-ring. The spring additionally pushes against a generally annular flat 77 of the collett rearward portion 74 to bias the collett 70 rearward towards a remainder of the drill/driver.

Figure 12A:
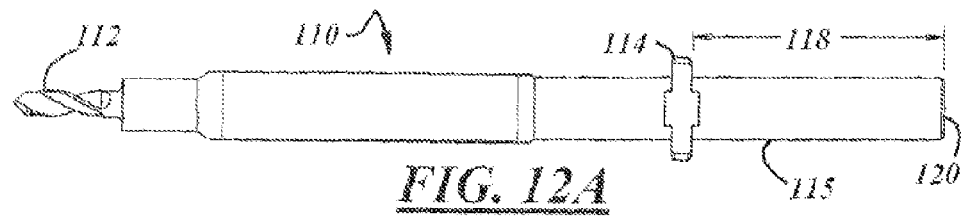
FIG. 12A is a side elevation view of a drill bit utilized with the collett shown in FIG. 4.
Figure 12B:
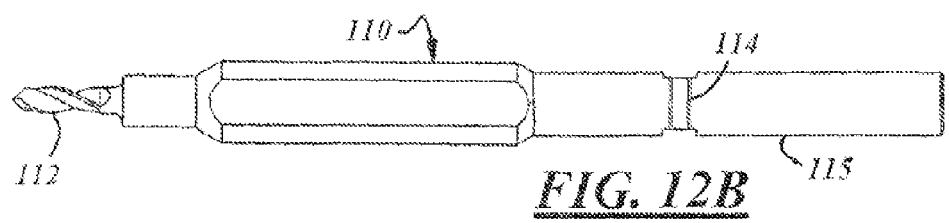
FIG. 12B is a top elevation view of a drill bit utilized with the collett shown in FIG. 4.
Figure 12C:
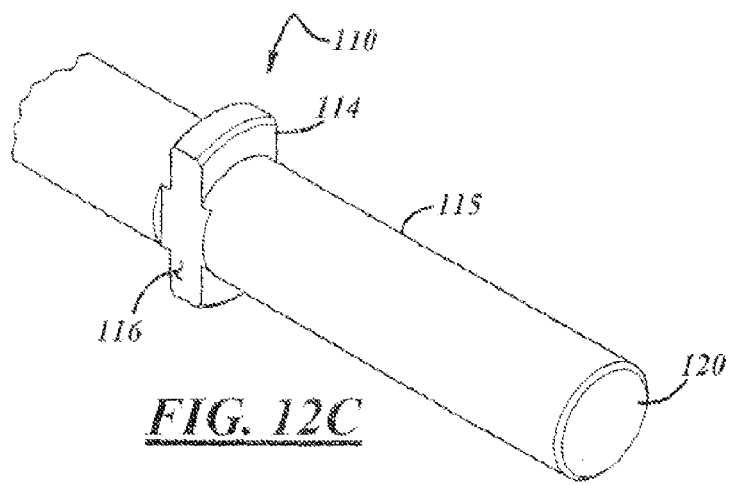
FIG. 12C is an enlarged perspective view of a portion of the drill bit shown in FIG. 12A.
Figure 13:
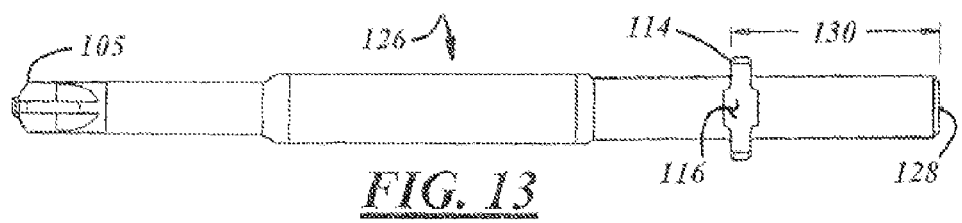
FIG. 13 is a side elevation view of a fastener driver utilized with the collett of FIG. 4 for metallic surgical screws.
Figure 14:
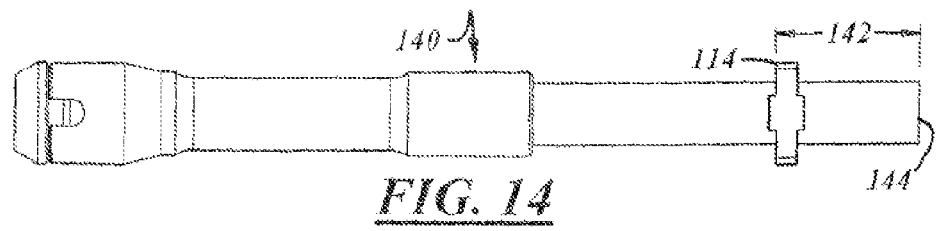
FIG. 14 is a driver for lactosorbic bits utilizing the collett of FIG. 4.
Figure 15:
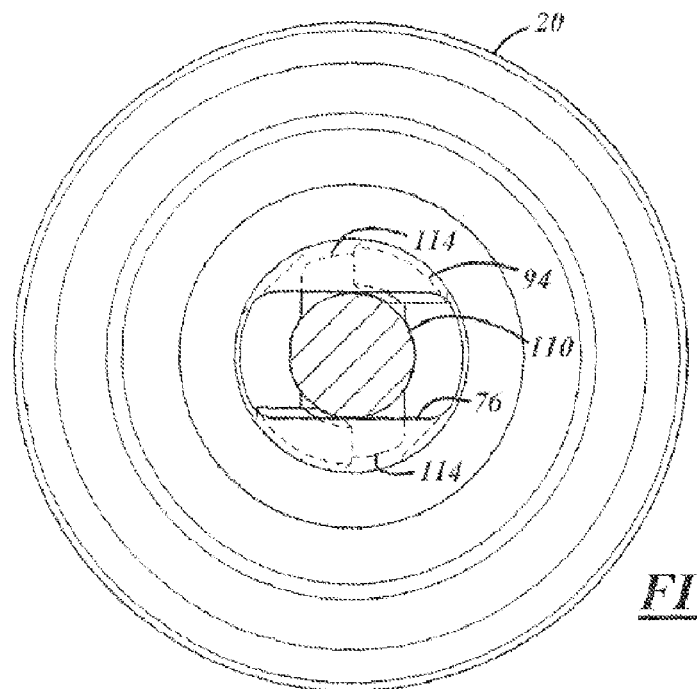
FIG. 15 is a front view of the collett shown in FIG. 4 illustrating a bit being installed within the collett.

Referring to FIGS. 12A, 12B and 12C, a drill bit 110 is shown with a distal working end 112 providing a drilling portion. The drill bit additionally has opposite radially projecting wings 114 having flats 116. The bit 110 has an identifier end portion 115 of a unique length 118 from a front of the intermediate wing 114 to its proximal end 120. End 120, upon installation with the drill/driver, abuts the plunger 92 as the identifier end 115 is installed within the bore 90 of the shaft 88. The length 118 is identified by afore described drill/driver sensor system informing the controller that a bit 110 is connected.

A metallic surgical screw driver bit 126 is provided having a torsional screw driver head 105. Bit 126 also has wings 114 with associated flats 116 and has a unique length 130 from the wings 114 to its end 128.

Another bit which can be utilized with the drill/driver 7 of the present invention is a lactosorbic driver bit 140. The lactosorbic driver bit 140 is utilized for driving a lactosorb surgical screw and again has wings 114 with a unique length 142 from the forward end of the wing 114 to bit end 144. Typically when using a lactosorbic bit the drill/driver 7 can have a time limiter that will turn off the drill/driver in exceptional cases wherein the lactosorbic screw does not shear as designed to keep the drill/driver 7 from burning up or otherwise malfunctioning. A more detailed review of the use of lactosorbic screws can be found by a review of Garcia et al., U.S. Patent Publication No. 2008/0215060 A1.

To connect one of the bits with the collett, the collett 70 is pulled forward against the force of the biasing spring (not shown). The end of a bit, for example, bit 110 with identifier end portion 115, is inserted within the collett window 76 with an angular orientation of the wings 114 such that the wings are generally aligned with the window 76. The bit end 120 contacts the plunger 92 and pushes the plunger back until the wings 114 contact a generally annular flat 150 of the shaft. The bit 110 is torqued bringing the wings 114 into their generally locked position within nest 96 of the stops 94 and are captured underneath the portion 98 of the stop. Upon release of the collett 70, the spring pushes the collett 70 rearward causing the triangular stops 82 to be positioned in contact with the wings 114 on an opposite side of the wings 114 from the nest 96 of the shaft, therefore locking the wings 114 of the bit 110 in both angular directions. The bit 110 is now ready for use. To change the bit 110, a surgeon need only to pull forward on the collett 70 and rotate the bit 110 bringing the bit's wings 114 out from their locked position underneath the stops 94 of the shaft and aligning the wings 114 with the window 76 of the collett for release.

Figure 16:
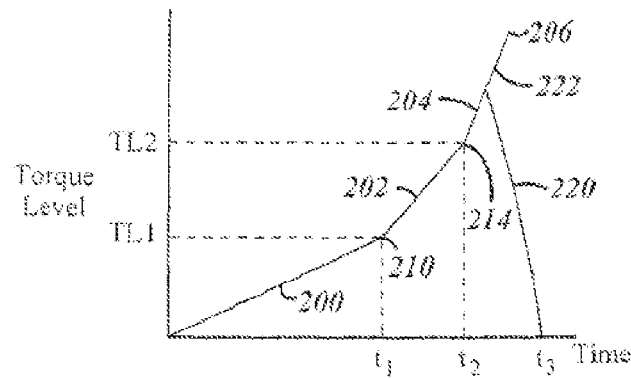
FIG. 16 is a graphic representation of a method utilizing the drill/driver according to the present invention illustrating the relationship between torque level and time.
Figure 17:
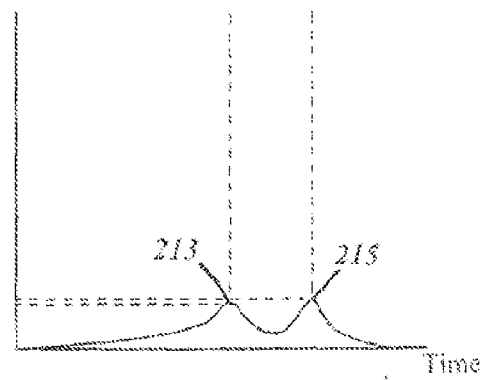
FIG. 17 is a graphic representation of the method of illustrating the relationship of torque level acceleration and time of the method represented in FIG. 16.
Figure 18:
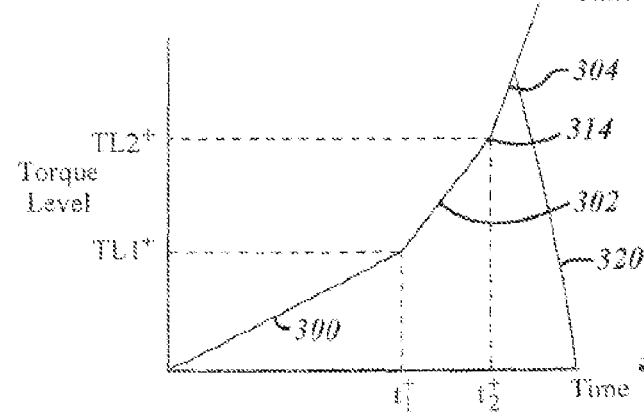
FIG. 18 is a view similar to that of FIG. 16 illustrating the aforementioned method of utilizing a larger surgical screw than that utilized in the generation of the relationship illustrated in FIG. 3.
Figure 19:
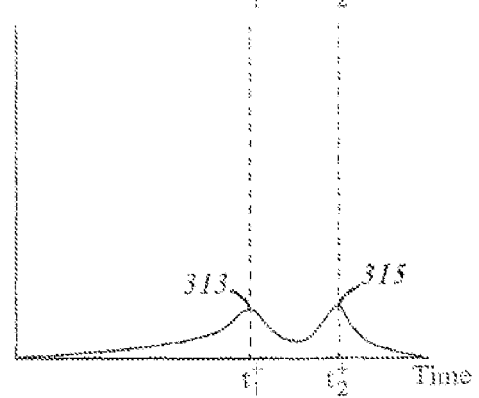
FIG. 19 is a graphic representation similar to that of FIG. 17 illustrating the relationship between torque level acceleration and time of the method represented in FIG. 18.
Figure 20:
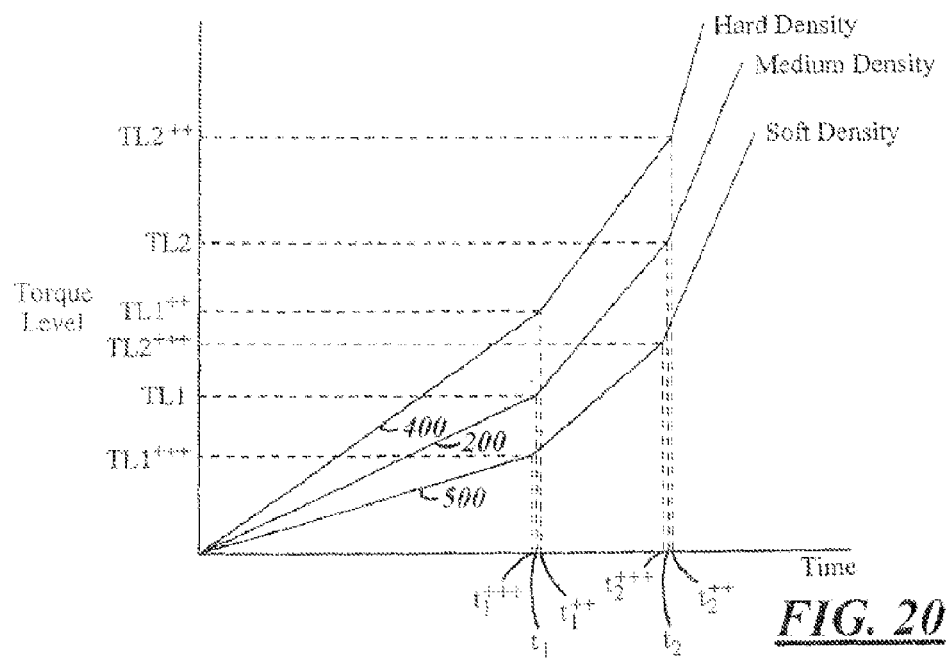
FIG. 20 is a view similar to that of FIG. 16 which additionally shows the relationship between torque level and time for multiple densities of bone.
Figure 21:
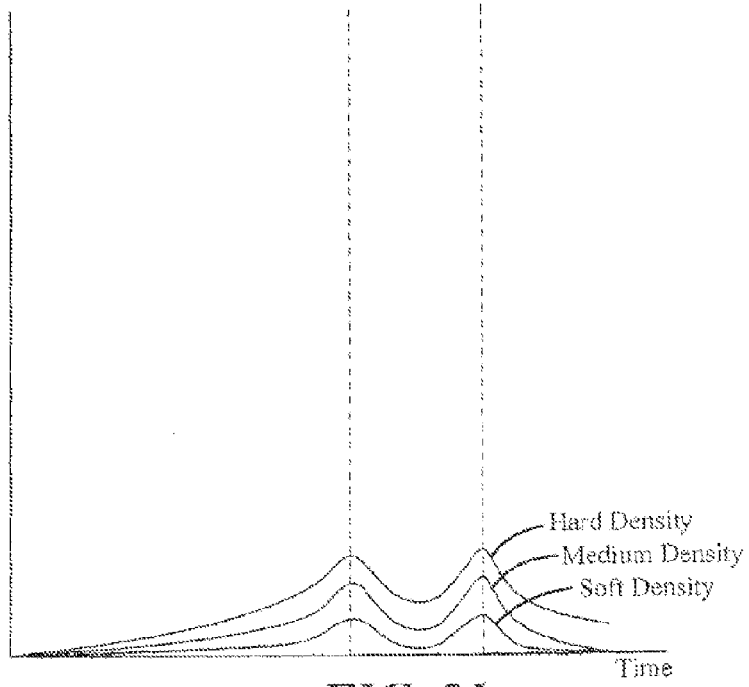
FIG. 21 is a graphical representation similar to that of FIG. 17 illustrating the relationship between torque level acceleration and time of the methods represented in FIG. 20.

Referring to FIGS. 16-21, a method of utilizing the surgical drill/driver 7 according to the present invention is provided. FIG. 16 is a graphic representation of torque level versus time. FIG. 17 is a graphic representation of the torque level acceleration versus time of the surgical drill/driver utilized in FIG. 16. FIG. 18 displays the torque level verses time characteristics of the same type of surgical screw utilizing the same driver that is utilized in FIG. 16. However in FIG. 18 the screw has an enlarged diameter and or enlarged length as compared with the screw utilized in FIG. 16. FIG. 19 is a graphic representation of the torque level acceleration versus time of the surgical drill driver utilized in FIG. 18. The middle line of FIG. 20 is a graphic representation of torque level versus time for the same screw and same bit utilized in developing the graphic representation of FIG. 16. Additionally in FIG. 20, graphic representations are given for torque level versus time when a patient has a higher or lower bone density than normal. FIG. 21 is a graphic representation of torque level acceleration versus time of the surgical drill/driver utilized in FIG. 20.

Referring to FIG. 16, the surgical drill/driver according to the present invention has approximately three stages of operation. The first stage of operation is initial thread insertion labeled 200 in FIG. 16. The second stage of operation is of that when a head of the surgical screw first contacts a plate. The second stage of operation is labeled 202. The third stage of operation of the surgical drill/driver labeled 204 is that of compression of the bone of the patient wherein the plate is being pressed against the patients' bone. Prior to the present invention, when manually torquing surgical screws to a patient by virtue of the tactile touch, the surgeon would realize when there was an increase of torque and hold up before there was strip out of the bone material. As mentioned previously, this manual method could possibly take five seconds or more of operation by the surgeon. With the drill/driver 7 according to the present invention, this process takes approximately 0.045 to 0.060 seconds (dependent upon screw size and patient bone density). More details on the fast screw insertion can be gained by a review of the aforementioned Garcia et al., U.S. Patent Publication. With the increased speeds of the drill/driver 7 (5000 RPM to 18,000 RPM), there is not enough time to manually turn off the drill/driver 7 to prevent an excessive torque level 206 that would cause strip out. Strip out torque levels 206 (FIG. 16) are not only dependent upon the size of the surgical screw utilized, but are also dependent upon the thickness and density of the patient's bone matter.

The graphic representation in FIG. 16 is that typically of a titanium surgical screw of 1.5 mm diameter and 4 mm or 5 mm in length. An example of such a screw a 91-6104 and 91-6105 screw manufactured by Biomet. As mentioned previously, section 200 represents initial thread insertion. At the end of initial thread insertion (time $t_1$), torque level is at TL1.

Referring to FIG. 17, there is a graph of torque level acceleration versus time in seconds. At the intersection between the thread insertion 200 and initial contact of the screw head with plate 202, there is an intersection 210. At intersection 210 and time "$t_1$", there is an initial peak 213 of torque level acceleration that is sensed and signaled to the controller of the drill/driver 7. After the surgical screw head hits the plate, the acceleration of torque level goes down although the actual torque level is increasing until the screw head and plate (bottom out) against the patient's body at intersection 214 (FIG. 16) causing a second peaking in torque level acceleration referred to as item 215 in FIG. 17. Peak 215 occurs at torque level TL2 at time $t_2$. At the second spike in output torque acceleration, the controller shuts off the surgical drill/driver 7 to prevent bone strip out. This causes the torque output to go to zero at time t3 along a path shown by line 220 rather than proceeding along portion 222 that would cause strip out at position 206. Position 206 is typically above 12-16 inch-ounces.

Referring to FIGS. 18 and 19, the graphical representation of torque level and torque level acceleration are provided for the same drill/driver 7 utilizing the same driver bit with the exception of a larger diameter screw and/or longer length screw. 2.0 mm×7.0 mm or 2.4 mm×16 mm. During the initial stage of thread insertion 300, since the surgical screw utilized in FIG. 18 is longer and or has a greater diameter than that shown in FIG. 16, both of these contribute to the time $t_1^*$ (for the initial insertion stage 300) being greater than the time $t_1$. The first spike in acceleration noted as 313 occurs at $t_1^*$. In the screw head to plate contact stage of operation 302 that is subsequent to the first spike 313 in torque level acceleration, the surgical screw head makes contact with the plate. At point 314 and at time $t_2^*$ there is a second spike 315 in the torque level acceleration that in the controller is cognizant of. Subsequent to the second spike 315 of torque acceleration, the drill/driver 7 enters into a compressive stage of operation noted as 304. At the aforementioned second spike 315 (time $t_2^*$) of torque acceleration, the controller 65 shuts off operation of the drill/driver 7 causing torque levels to crash along line 320 preventing the bone mass strip out. It is significant to note that the torque level TL2\* is are typically greater than TL2 due to the increased demands for torque level output due to the increased diameter and/or length of the surgical screw used in the operation in FIGS. 18 and 19.

Referring to FIGS. 20 and 21, the torque level versus time and torque level acceleration verses time graphic charts are given for using the surgical drill/driver 7 with the same driver bit as utilized in FIGS. 16 and 17 as provided. Also in FIGS. 20 and 21, the same size surgical screw is being utilized. In FIG. 20, the middle line is identical to that of FIG. 16 and represents the surgical screw being applied to a patient with a bone having medium density. The upper line is for the surgical screw being applied to a patient with a bone mass with a higher density. The lower line is for the surgical screw being applied to a patient with a damaged, thinner or lower bone density and/or bone mass. In the case of high density bone, the time $t_1^{}$ required for thread insertion 400 is greater than that of $t_1$. Accordingly, the absolute torque level TL1**\*\* is greater than that of TL1 and additionally the torque level TL2\*\* of the drill/driver 7 shut off is higher than the torque level TL2 in the medium density bone mass. In case of lower bone density, the time $t_1^{*}$ required for thread insertion 500 is less than that of $t_1$. Accordingly, the absolute torque level TL1**\*\*\* is less than that of TL1 and additionally the torque level TL2\*\*\* of drill/driver shut off is lower than the torque level TL2 at shut off in the stronger medium density bone mass. Accordingly, by utilizing the detected second spike in torsional acceleration to control shut off of, the drill/driver 7 of the present invention can operate in very short time spans at very high speeds. The drill/driver 7 automatically adjusts shut off to prevent bone strip out for the same bit, regardless of the screw dimension or bone condition.

When utilizing the drill/driver 7 of the present invention, the battery is first placed inside of the drill/driver. An LED (light emitting diode) button turns on to indicate to the surgeon that power is flowing to the drill/driver 7. The collet 28 (or 70) is pulled forward to load a desired bit or drill into the same. If the drill/driver utilized for driving a screw, a screw is loaded to the driver from a tray (not shown). A plate (not shown) is placed against the patient's bone and the tip of the screw is contacted against the patient's bone through a hole in the plate. The drill/driver 7 is configured so that a pressure force must be applied against the screw by the drill/driver 7 of approximately two pounds or the trigger 24 is inoperative to start the drill/driver 7. The two pounds of force are required so that the screw propels forward during the insertion state. It should be noted that in the drilling mode, a pressure force upon the patient's body by drill/driver 7 is not required. When the trigger 24 is fired (in the driving mode), the control system (typically located on a circuit board within the drill/driver) begins to look for torque changes and executes tasks as commanded as previously explained. Upon completion of insertion of the screw, the drill/driver 7 is removed and the next screw is loaded to the drill/driver and the task is repeated.

Figure 22:
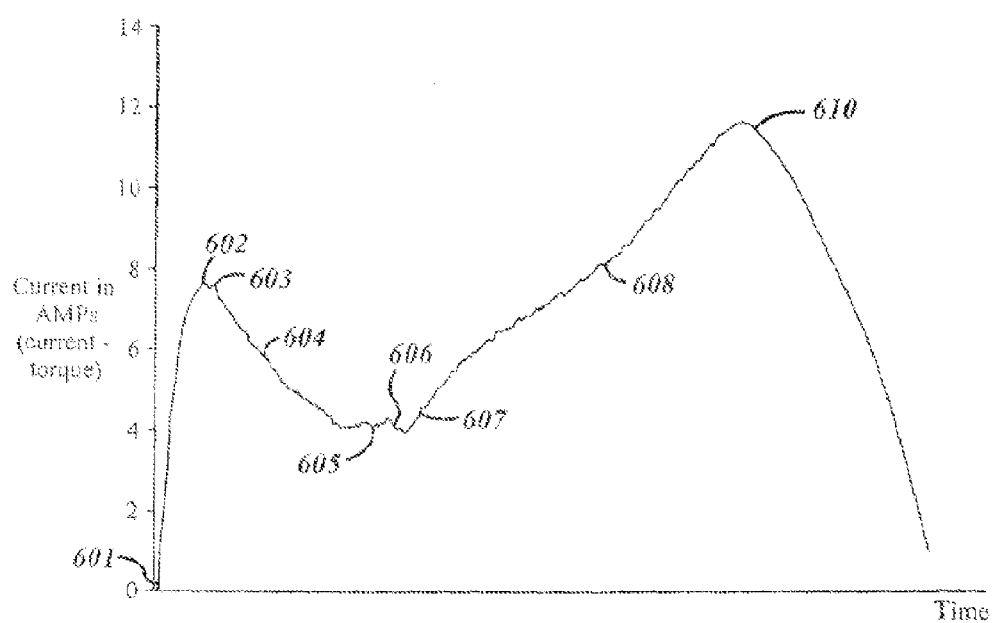
FIG. 22 is a graphical representation of another preferred embodiment method utilizing the drill/driver according to the present invention.

FIG. 22 is a graphic representation of a method of utilization of the drill/driver 7 of the current invention that illustrates the relationship between torque level and time. At time equals zero (0), the drill driver 7 as mentioned previously, is preloaded against the patient's bone matter to allow for the trigger 24 to be responsive to the surgeon's activation. At point 601 there is an immediate rise in current (torque level) as the motor 11 starts to rotate. This torsional force peaks at position 602 as the screw starts an initial turning. At point 603 as torque begins to diminish the controller recognizes that there has been a first peak of torque level. As the motor continually picks up speed and before the tip of the screw bites into the bone matter, there is an initial slide in torque level noted as portion 604. As the self drilling surgical screw initially bites into the bone matter, there is a short stage of virtually constant torque level noted in portion 605 of the graphic representation of FIG. 22. After initial grabbing into the bone by the tip of the surgical screw, there is a subsequent initial stripping out the bone matter along the inner diameter of the surgical screw. This strip out is not the strip out of the tap threads into the bone matter as when the screw is fully fastened to the patient's bone matter, but is the strip out which occurs at the very tip of the screw. This phenomenon causes a slight lowering of the torque level that is shown graphically in portion 606 of the graphic representation of FIG. 22. After the initial strip out of the bone matter caused by the tip of the threaded fastener, there is a constant rise in torque level as the screw penetrates the bone matter of the patient. At point 607, there is a recognition that this rise has occurred to a point that a valley in torque level has occurred as compared with portions 604, 605 and 606 of the torque level graphic representation. At this point, the controller is cognizant that the threaded fastener is penetrating into the patient's bone and also tapping the appropriate threaded path within the patient's bone. The above noted process continues along section 608 and thereafter peak at point 610. At point 610, the first derivative of torque level turns negative as the fastener approaches a strip out condition in the patient's bone matter wherein after the controller cuts off current to the motor 11 to prevent strip out from occurring. It is apparent to those skilled in the art that a graph similar to that as shown in FIG. 22 will be slightly above the graph of FIG. 22 or below the graph of FIG. 22 depending upon different conditions of bone density as previously described in relationship with the graph of FIG. 20.

The description of the invention is merely exemplary in nature and, thus, variations that do not depart from the gist of the invention are intended to be within the scope of the invention. Such variations are not to be regarded as a departure from the spirit and scope of the invention.

What is claimed is:

1. A surgical drill comprising:
   a body mounting a motorized shaft with a connected driver bit for driving a surgical screw; and
   control circuitry configured to:
   monitor a torque level output of the surgical drill;
   determine that the surgical drill is in a thread insertion stage of operation prior to a first spike in output torque acceleration;
   determine that the surgical drill is in a surgical screw head to object contact stage of operation subsequent to the first spike in output torque level acceleration and prior to a second spike in output torque acceleration; and
   determine whether the surgical drill is in a compression stage of operation subsequent to the second spike in output torque acceleration; and
   shut off the surgical drill to prevent strip out of the surgical screw head in response to determining that the surgical drill is in the compression stage of operation subsequent to the second spike in output torque level acceleration.

2. The surgical drill of claim 1, wherein monitoring the output torque level comprises monitoring a current level of a motor powering the motorized shaft of the surgical drill.

3. The surgical drill of claim 1, wherein the surgical screw is a self-tapping surgical screw.

4. The surgical drill of claim 1, wherein the surgical screw is a self-drilling surgical screw.

5. The surgical drill of claim 1, wherein the control circuitry is configured to shut off the surgical drill in response to determining that the surgical drill is in the compression stage of operation irrespective of a manual command to the surgical drill.

6. The surgical drill of claim 1, wherein the surgical drill is further configured to attach the surgical screw to anatomy of a patient using the connected driver bit.

7. The surgical drill of claim 6, wherein the control circuitry is further configured to detect a head of the connected driver bit making contact with the surgical screw in response to determining that the surgical drill is at the first spike in output torque acceleration.

8. A surgical drill comprising:
   a body mounting a motorized shaft with a connected driver bit for driving a surgical screw; and
   control circuitry configured to:
   monitor a torque level output of the surgical drill;
   determine a first peak in output torque level;
   determine a first valley in output torque level subsequent to the first peak in output torque level;
   determine a negative first derivative in output torque level subsequent to the first valley in output torque level;
   shut off the surgical drill in response to determining the negative first derivative in output torque level subsequent to the first valley in output torque level to prevent strip out of the surgical screw.

9. The surgical drill of claim 8, wherein monitoring the torque level output comprises monitoring a current level of a motor powering the motorized shaft of the surgical drill.

10. The surgical drill of claim 8, wherein the surgical screw is a self-tapping surgical screw.

11. The surgical drill of claim 8, wherein the surgical screw is a self-drilling surgical screw.

* * * * *